United States Patent [19]

Voss et al.

[11] 4,294,959
[45] Oct. 13, 1981

[54] SELECTIVELY PROTECTED 4,6-DI-O-(AMINOGLYCOSYL)-1,3-DIAMINOCYCLITOLS AND THEIR PRODUCTION

[75] Inventors: Eckart Voss, Cologne; Uwe Petersen, Leverkusen; Peter Stadler, Haan, all of Fed. Rep. of Germany

[73] Assignee: Bayer Aktiengesellschaft, Leverkusen, Fed. Rep. of Germany

[21] Appl. No.: 74,047

[22] Filed: Sep. 10, 1979

[30] Foreign Application Priority Data

Sep. 20, 1978 [DE] Fed. Rep. of Germany ..... 28409076

[51] Int. Cl.³ .................... C07H 17/00; C07H 15/22
[52] U.S. Cl. ................................. 536/17 R; 424/180
[58] Field of Search ............................... 536/17 R, 10

[56] References Cited

U.S. PATENT DOCUMENTS

| 4,000,261 | 12/1976 | Daniels | 536/10 |
| 4,020,269 | 4/1977 | Hiraga et al. | 536/10 |
| 4,029,883 | 6/1977 | Hiraga et al. | 536/17 R |
| 4,062,947 | 12/1977 | Wright et al. | 536/17 R |
| 4,063,015 | 12/1977 | Mallams | 536/17 R |
| 4,117,221 | 9/1978 | Daniels | 536/10 |

Primary Examiner—Delbert R. Phillips
Assistant Examiner—Blondel Hazel
Attorney, Agent, or Firm—Sprung, Felfe, Horn, Lynch & Kramer

[57] ABSTRACT

The invention relates to selectively protected 4,6-di-O-(aminoglycosyl)-1,3-diamino cyclitols (and methods for their preparation) useful as intermediates for the synthesis of antibiotics, such as those of the sisomycin type.

11 Claims, No Drawings

SELECTIVELY PROTECTED 4,6-DI-O-(AMINOGLYCOSYL)-1,3-DIAMINOCYCLITOLS AND THEIR PRODUCTION

The invention relates to new, selectively protected 4,6-di-O-(aminoglycosyl)-1,3-diaminocyclitol compounds and to a process for their production. The compounds may be used as intermediates for the synthesis of valuable new and known antibiotics.

According to the present invention there are provided compounds which are 4,6-di-O-(aminoglycosyl)-1,3-diaminocyclitols of the following general formula

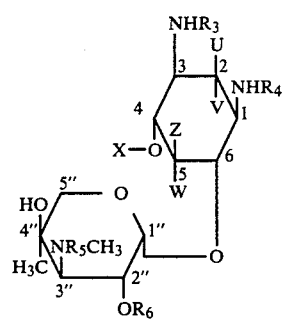

in which
X denotes a radical of the general formula

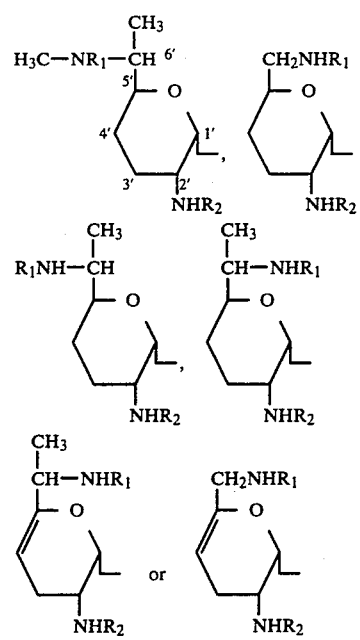

U, V, W and Z independently denote a hydrogen atom or a hydroxyl group,
U and V, and W and Z not simultaneously denoting OH,
$R_1$, $R_2$ and $R_3$ denote —CO—A,
$R_4$ denotes a hydrogen atom,
$R_5$ denotes a radical —$SR_7$ and
$R_6$ denotes a hydrogen atom or a space-filling substituent which can be split off,
and in which
A denotes a radical of the formula

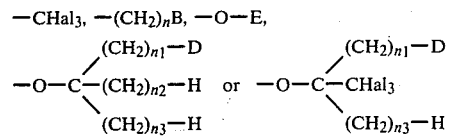

B and D denote a hydrogen atom or an optionally substituted phenyl group,
E denotes an optionally substituted phenyl group,
n is 0, 1, 2, 3, 4 or 5,
$n_1$, $n_2$ and $n_3$ are independently 0, 1, 2, 3, 4 or 5, Hal denotes a fluorine, chlorine or bromine atom and
$R_7$ denotes an optionally substituted phenyl, diphenylmethyl or triphenylmethyl group.

Examples of suitable substituents of the optionally substituted phenyl, diphenylmethyl or triphenylmethyl radicals $R_7$ are 1, 2 or 3 substituents selected from trifluoromethyl, nitro, $C_1$ to $C_4$ alkyl, $C_1$ to $C_4$ alkoxy, ($C_1$ to $C_4$ alkoxy)-carbonyl and phenyl, or 1 to 5 halogen atoms, preferably chlorine atoms. Examples of -$SR_7$ groups which may be mentioned are o-nitrophenylsulphenyl and 2,4,5-trichlorophenylsulphenyl.

Suitable substituents of the optionally substituted phenyl radicals B, D and E are 1 or 2 substituents selected from nitro, halogen, preferably chlorine, $C_1$ to $C_4$ alkyl, $C_1$ to $C_4$ alkoxy and phenyl.

Examples of space-filling radicals $R_6$ which can be split off are those of the formula

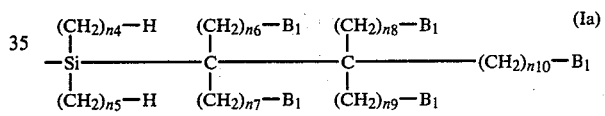

or

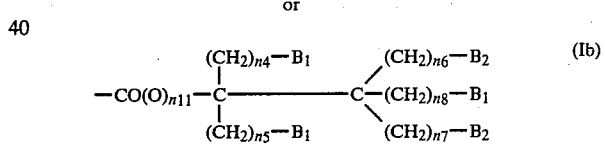

in which
$n_4$, $n_5$, $n_6$, $n_7$, $n_8$, $n_9$ and $n_{10}$ are independently 0, 1, 2 or 3,
$n_{11}$ is 0 or 1,
$B_2$ has any of the meanings given for B or denotes a $C_1$ to $C_5$ alkoxy or $C_3$ to $C_5$ alkenyloxy group and
$B_1$ has any of the meanings given for B.

The following silyl groups (Ia) are particularly valuable: dimethyl-(1,2-dimethylpropyl)-silyl, dimethyl-(2,4,4-trimethylpentyl)-silyl, dimethyl-(1,1,2-trimethylpropyl)-silyl, dimethyl-(2-methyl-2-phenylethyl)-silyl, dimethyl-(1,1,4,4-tetramethylbutyl)-silyl and dimethyl-[2-methyl-2-(4-methylcyclohex-3-enyl)-ethyl]-silyl.

The N-protected compounds of formula (I) according to the invention which are derived from the antibiotics gentamicin $C_1$, gentamicin $C_{1a}$, gentamicin $C_2$, gentamicin $C_{2a}$, gentamicin $C_{2b}$, sisomicin, verdamicin, G 52, mutamicin 1, mutamicin 2, mutamicin 4 and mutamicin 6 are of particular interest.

Of these, the derivatives of sisomicin represented by the formula (II)

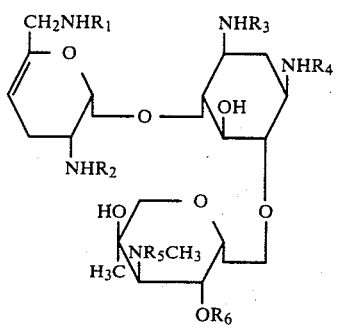

in which

R₁, R₂, R₃, R₄, R₅ and R₆ have the meanings indicated above, are particularly valuable.

According to the present invention we further provide a process for the production of compounds of the present invention in which a compound of the formula (I) in which $R_1$, $R_2$, $R_3$, $R_4$ and $R_5$ denote a —$SR_7$ group, $R_6$ denotes a hydrogen atom and U, V, W, Z and $R_7$ have the above-mentioned meanings, is subjected to the following steps:

1. reaction with a silylating agent or an acylating agent of the general formula $$R_6—G \qquad (III)$$

in which $R_6$ has the meaning given in the definition of formula (I), with the exception of a hydrogen atom, and G denotes a leaving group for this reaction step, 2. splitting off the —S—$R_7$ groups $R_1$, $R_2$, $R_3$ and, if appropriate, $R_4$, 3. acylating the amino groups liberated, with the exception of the 1—NH₂ group if this has already been liberated in step 2, with an acylating agent of the general formula $$A—CO—G \qquad (IV)$$

in which

A has the meaning given above and

G denotes a leaving group for the acylation, 4. splitting off the S—$R_7$ group $R_4$, if this has not been effected in step 2, and, if appropriate, 5. splitting off the space-filling substituent $R_6$, it being possible to change the sequence of steps 4 and 5.

Suitable leaving groups G are, for example, halogen, in particular chlorine, and perfluorobutylsulphonyloxy in the case of silylation, and, for example, halogen, an activating ester radical, such as p-nitrophenoxy, or a radical A—CO—O, A having the meaning given above, in the case of acylation.

The silylation in step 1. is preferably carried out in an inert solvent, such as, chlorinated alkane, e.g. methylene chloride or chloroform, in the presence of a catalyst, which at the same time is the auxiliary base required for bonding the acid liberated. All the organic bases which activate the Si-G bond are suitable for this. The reaction is preferably carried out with equivalent amounts of imidazole as the catalyst base. The silylating agent and catalyst base can in each case be reacted in stoichiometric amounts with the compound of the formula (I) in which $R_1$, $R_2$, $R_3$, $R_4$ and $R_5$ denote —S—$R_7$, but considerably shorter reaction times are achieved with a 2-fold–5-fold excess of silylating agent. The reaction temperature is preferably 0°–80° C., more preferably 20°–40° C.

If acid anhydrides or activated esters are used, the acylation in step 1. is preferably carried out in basic solvents, more preferably in pyridine, with a 1-fold–10-fold, preferably 3-fold–5-fold, excess of acylating agent in the temperature range of preferably 0°–80° C., more preferably 10°–30° C. If acid halides are used as the acylating agents, these are reacted in stoichiometric amounts or in a 2-fold–3-fold excess preferably in an inert solvent, such as methylene chloride, in the presence of equivalent amounts of an organic auxiliary base, for example a tri-$C_1$-$C_4$-alkyl amine, such as triethylamine, preferably at 0°–40° C., more preferably at 10°–30° C. The reaction times are considerably reduced by adding 10-20 mol % of a catalyst, such as p-dimethylaminopyridine or p-pyrrolidino-pyridine.

Preferably, in step 2, the protective groups S—$R_7$ are split off by reaction with nucleophiles, preferably with nucleophiles containing H—S groups, such as H₂S, thiophenol or 2-mercaptobenzthiazole, at 0°–20° C. in a suitable inert organic solvent, such as methylene chloride or methanol or in mixtures of such solvents.

The amount of agent to be employed for the splitting off reaction depends on its reactivity; in most cases it is employed in a 2-fold-5-fold excess. Splitting off the S—$R_7$ groups $R_1$, $R_2$ and $R_3$ without splitting off the S—$R_7$ groups $R_4$ and $R_5$ can easily be achieved by changing to shorter reaction times and/or lower temperatures for the splitting off reaction and/or a smaller excess of nucleophile.

The acyl groups CO—A are introduced by generally customary methods, such as are described, for example, in Houben-Weyl, Methoden der organischen Chemie (Methods of Organic Chemistry), Volume XV, Georg Thieme-Verlag, Stuttgart 1974. The choice of acyl groups CO—A depends on the further reactions for which the interemediate products according to the invention are to be employed.

If the S—$R_7$ protective group $R_4$ has already been split off in the second reaction stage, the acyl groups $R_1$, $R_2$ and $R_3$ must be introduced selectively so that the 1—NH₂ group which is shielded by the steric influence of the space-filling substituent $R_6$ is not attacked. The reactive esters of the acids A—COOH, such as the p-nitrophenyl esters or the N-hydroxysuccinimide esters, for example, are successfully used in this case.

The protective group $R_6$ is preferably split off, and preferably at room temperature, either in water-immiscible inert organic solvents, such as methylene chloride, using tetraalkylammonium fluorides, for example tetrabutylammonium fluoride, or in dimethylsulphoxide/water mixtures, either using inorganic fluorides, such as potassium fluoride, or using inorganic bases, such as alkali metal hydroxide, e.g. sodium hydroxide solution.

The intermediate products of the formula (I) according to the invention are used for the preparation of 4,6-di-O-(aminoglycosyl)-1,3-diaminocyclitols which are substituted on the 1-NH₂ group, in particular of derivatives of the antibiotics gentamicin $C_1$, gentamicin $C_{1a}$, gentamicin $C_2$, gentamicin $C_{2a}$, gentamicin $C_{2b}$, sisomicin, verdamicin, G 52, mutamicin 1, mutamicin 2, mutamicin 4 and mutamicin 6.

These antibiotics are valuable substances for effectively combating bacterial infections. However, their high activity is frequently associated with a relatively high nephrotoxicity and ototoxicity; the germs combated also develop resistance. For these reasons, it is desirable to prepare derivatives of the aminoglycoside antibiotics with improved properties which, with a reduced toxicity, if necessary also enable resistant germs to be combated. Compounds such as 1-N-acetylsisomicin and 1-N-ethylsisomicin have been disclosed as substances with properties which have been improved in this way (DT-OS (German Published Specification) No. 2,437,160).

However, the preparation of mono-N-substituted sisomicin derivatives starting from unprotected sisomicin proves difficult, since five amino groups of comparable reactivity are present in the sisomicin molecule. Reaction product mixtures are thus always obtained, and these necessitate expensive chromatography processes to isolate the desired compound.

The present invention provides a process for the preparation of derivatives of aminoglycoside antibiotics with a selectively unprotected amino group, the nature of the protective groups being such that both alkylation reactions and acylation reactions on the free nitrogen atoms are possible and subsequent gentle deblocking can be carried out.

A further advantage of the process according to the invention is that throughout the entire synthesis route, a chromatographic purification operation of the intermediate products is not necessary and the synthesis can thus also be applied on an industrial scale.

The following Examples illustrate the preparation of intermediate compounds of the present invention.

EXAMPLE 1

Penta-N-(o-nitrophenylsulphenyl)-sisomicin

A solution of 240 g of o-nitrophenylsulphenyl chloride in 900 ml of dioxane, and 390 ml of 4 N NaOH are simultaneously added to 166.1 g of sisomicin sulphate in 300 ml of 4 N NaOH and 1,350 ml of dioxane in a manner such that a pH of 12–14 is maintained. The precipitate is filtered off and discarded, the filtrate is stirred into 5 l of water and the yellow amorphous precipitate is filtered off, washed with 150 ml of methanol and dried. Yield: 290 g (100% of theory) of crude product, which is employed for the subsequent reactions without further purification. A pure product is obtained after chromatography on silica gel with a running agent mixture $CH_2Cl_2/CH_3OH = 97.5/2.5$.

$R_F = 0.62$ ($CH_2CH_2/CH_3OH = 97.5/2.5$)

13-C-NMR ($CDCl_3$): $\delta = 124$–148 (aromatic C); 102.3 (C-1''); 99.0 (C-1'); 97.92 (C-4'); 89.05 (C-6); 82.33 (C-4); 53.31 (C-1); and 56.73 (C-3) ppm

EXAMPLE 2

Penta-N-(o-nitrophenylsulphenyl)-2''-O-[dimethyl-(1,2-dimethylpropyl)-silyl]-sisomicin 60.6 g of crude penta-N-(o-nitrophenylsulphenyl)-sisomicin and 8.75 g of imidazole are dissolved in 250 ml of absolute methylene chloride. 22.5 ml of dimethyl-(1,2-dimethyl-propyl)-silyl chloride are added dropwise at 0° C., with exclusion of moisture. The mixture is evaporated to about 170 ml in vacuo and left to stand at room temperature for 48 hours. After adding 130 ml of absolute methylene chloride, the precipitate is filtered off, the filtrate is thoroughly shaken vigorously with 350 ml of petroleum ether and the petroleum ether phase is decanted off and discarded. The oil which has separated out is dissolved in 100 ml of methylene chloride, separated out again with 250 ml of petroleum ether and finally dried under a high cvacuum. Yield: 60 g (89%) of crude product, which is employed for the subsequent reactions without further purification. A pure product is obtained by chromatography on silica gel with $CH_2Cl_2/CH_3OH = 99/1$.

$R_F$ ($CH_2Cl_2/CH_3OH = 99.5/0.5$): 0.62

13-C-NMR($CDCl_3$): $\delta = 124$–138 (aromatic C); 147.54 (C-5'); 102.26 (C-1''); 97.81 (C-4'); 99.09 (C-1'); $-2.9$ to $-3.0$ (Si—$CH_3$);

22.77 (Si—CH—); and 30.60 (Si—CH—CH) ppm

Penta-N-(o-nitrophenylsulphenyl)-2'',5-bis-O-[dimethyl-(1,2-dimethyl-propyl)-silyl]-sisomicin is isolated as a by-product.

$R_F$ ($CH_2Cl_2/CH_3OH = 99.5/0.5$): 0.79

13-C-NMR ($CDCl_3$): $\delta = 124$–146 (aromatic C), 148.00 (C-5'): and 96.13 (C-4') ppm

EXAMPLE 3

Penta-N-(o-nitrophenylsulphenyl)-2''-O-(2-ethylhexanoyl)sisomicin 15 ml of triethylamine and 1.5 g of p-dimethylaminopyridine are added to 60.6 g of crude penta-N-(o-nitrophenylsulphenyl)-sisomicin in 250 ml of absolute methylene chloride. 13 ml of 2-ethyl-hexanoyl chloride in 25 ml of absolute methylene chloride are added dropwise to this mixture at 0° C. After 20 hours at room temperature, the mixture is extracted by shaking twice with 50 ml of $H_2O$ each time, the organic phase is dried with $Na_2SO_4$ and the product is isolated by precipitating with petroleum ether. The yield of crude product after drying under a high vacuum is quantitative.

A pure product is obtained by chromatography on silica gel with $CH_2Cl_2/CH_3OH$-99/1.

$R_F$ ($CH_2Cl_2/CH_3OH = 99.5/0.5$): 0.41

13-C-NMR ($CDCl_3$); $\delta = 124$–146 (aromatic C); 175.77 (CO);

53.22 (CO—CH—);

99.73 (C-1''); 99.13 (C-1'); 97.95 (C-4'); 147.75 (C-5'); 82.13 (C-4); 76.47 (C-5), 88.98 (C-6); 69.30 (C-2''); 70.89 (C-4''); and 68.06 (C-5'') ppm

EXAMPLE 4

Penta-N-(o-nitrophenylsulphenyl)-2''-O-butyryl-sisomicin 10 g of crude penta-N-(o-nitrophenylsulphenyl)-sisomicin are left to stand with 33 ml of pyridine and 60 ml of butyric anhydride at 20° C. for 48 hours, the mixture is evaporated under a high vacuum, the residue is taken up in methylene chloride and the product is precipitated with petroleum ether. The yield of crude product is quantitative. A pure product is obtained by chromatography with $CH_2Cl_2/CH_3OH = 99/1$ on silica gel:

$R_F$ ($CH_2Cl_2/CH_3OH = 99/1$): 0.46

13-C-NMR (CDCl$_3$): δ=172.94 (CO); 147.82 (C-5'); 99.96 (C-1''); 99.19 (C-1'); and 98.03 (C-4') ppm Penta-N-(o-nitrophenylsulphenyl)-2'',5-bis-O-butyrylsisomicin is isolated as a by-product.

R$_F$ (CH$_2$Cl$_2$/CH$_3$OH=99/1): 0.65

13-C-NMR (CDCl$_3$): δ=172.30 and 173.27 (in each case CO); 148.07 (C-5'); 100.46 (C-1''); 98.42 (C-1'); and 98.02 (C-4') ppm

EXAMPLE 5

Penta-N-(o-nitrophenylsulphenyl)-2''-O-isovaleryl-sisomicin 7.2 ml of triethylamine and 720 mg of 4-dimethylaminopyridine are added to 24.24 g of penta-N-(o-nitrophenylsulphenyl)-sisomicin in 100 ml of absolute methylene chloride. 4.8 ml of isovaleryl chloride in 5 ml methylenechloride are added dropwise at 0° C. After 20 hours at room temperature, the mixture is worked up analogously to Example 3.

The yield of crude product is quantitative.

R$_F$ (CH$_2$Cl$_2$/CH$_3$OH=99/1: 0.46

EXAMPLE 6

1,3''-Bis-N-(o-nitrophenylsulphenyl)-2''-O-[dimethyl-(1,2-dimethyl-propyl)-silyl]-sisomicin 16 g of 2-mercapto-benzthiazole are added to 56 g of crude penta-N-(o-nitrophenylsulphenyl)-2''-O-[dimethyl-(1,2-dimethyl-propyl)-silyl]-sisomicin in 36 ml of methylene chloride/70 ml of methanol, the mixture is shaken until a clear solution is obtained and the solution is left to stand at 5° C. for 2 hours. The precipitate which thereby separates out is filtered off and the solution is used for the further reactions without isolating the desired product. The yield is about 80% of theory. In order to prepare a pure product, the filtrate is evaporated rapidly in vacuo and the residue is chromatographed on silica gel with (a) methylene chloride, (b) methylene chloride/CH$_3$OH (8:2) and (c) with CH$_2$Cl$_2$/CH$_3$OH/20% strength aqueous ammonia (7:2.7:0.3). The yield of pure product is 25.3 g (69%) R$_F$ (CH$_2$Cl$_2$/CH$_3$OH/20% strength aqueous NH$_3$=7:2.7:0.3)=0.66

13-C-NMR (CD$_3$OD): δ=1.5 (Si-CH$_3$); 122-146 (aromatic C); 147.14 (C-5'); 103.31 (C-1''); 100.16 (C-1') and 99.30 (C-4') ppm 3 g (10%) of 3''-N-(o-nitrophenylsulphenyl)-2''-O-[dimethyl-(1,2-dimethyl-propyl)-silyl]-sisomicin are isolated as a by-product during the column chromatography. R$_F$ (CH$_2$Cl$_2$/CH$_3$OH/20% strength aqueous NH$_3$=7:2.7:0.3)=0.15

13-C-NMR (CD$_3$OD): δ=76.66 (C-2''); 21.70 (C-6'); 30-40 (N-CH$_3$); 53.13 (C-1), 52.18 (C-3); 44.06 (C-6') and 49.41 (C-2') ppm

EXAMPLE 7

1,3''-Bis-N-(o-nitrophenylsulphenyl)-2''-O-butyryl-sisomicin 10 g of crude penta-N-(o-nitrophenylsulphenyl)-2''-O-butyryl-sisomicin in 117 ml of methylene chloride/58 ml of methanol are shaken with 7 g of 2-mercaptobenzthiazole until a clear solution has formed and the solution is left to stand at 5° C. for 2 days. After filtering off the precipitates, the filtrate is further processed without isolating the desired product. R$_F$ (CH$_2$Cl$_2$/CH$_3$OH/20% strength aqueous NH$_3$ 3.5:1.35:0.15)=0.45

EXAMPLE 8

1,3''-Bis-N-(o-nitrophenylsulphenyl)-2''-O-isovaleryl-sisomicin 48 g of crude penta-N-(o-nitrophenylsulphenyl)-2''-O-isovaleryl-sisomicin are shaken with 120 ml of methylene chloride, 120 ml of methanol and 27 g of 2-mercaptobenzthiazole until a clear solution has formed and the solution is then left to stand at 5° C. for 2 hours. The precipitate is filtered off, the filtrate is evaporated rapidly in vacuo, the residue is taken up in methylene chloride, the solution is extracted by shaking twice with water and dried over Na$_2$SO$_4$, the product is precipitated with ether and the precipitate is dried in vacuo. Crude yield: 23 g (74%). A purified substance is obtained by chromatography on silica gel by the methods described for Example 6.

R$_F$ (running agent as Example 7)=0.46

EXAMPLE 9

1,3''-Bis-N-(o-nitrophenylsulphenyl)-2''-O-(2-ethylhexanoyl)-sisomicin 16 g of crude penta-N-(o-nitrophenylsulphenyl)-2''-O-(2-ethylhexanoyl)-sisomicin are shaken with 40 ml of methylene chloride, 40 ml of CH$_3$OH and 9 g of 2-mercaptobenzthiazole until a clear solution has formed, which is left to stand at 5° C. for 7 hours. The precipitate is filtered off and the filtrate is evaporated rapidly in vacuo. Purification is carried out analogously to Example 6, by chromatography on silica gel. The yield is 6.6 g (63% of theory).

R$_F$ (running agent as Example 7)=0.58

13-C-NMR (CD$_3$OD): δ=177.13 (CO); 151.14 (C-5'); 124-146 (aromatic C); 101.06 (C-1' and C-1''); 96.57 (C-4'); and 71.17 (C-2'') ppm

EXAMPLE 10

1,3''-Bis-N-(o-nitrophenylsulphenyl)-2',3,6'-triacetyl-2''-O-[dimethyl-(1,2-dimethyl-propyl)-silyl]-sisomicin 15 ml of acetic anhydride and 38 ml of 6 N NaOH are added to the crude solution of 1,3''-bis-N-(o-nitrophenylsulphenyl)-2''-O-[dimethyl-(1,2-dimethyl-propyl)-silyl]-sisomicin in the course of 2 minutes, whilst cooling with ice, in a manner such that the reaction mixture always remains alkaline. The mixture is evaporated in vacuo and until the red oil settles as a clear liquid. The aqueous phase is decanted off and the oil is stirred with 120 ml of H$_2$O at 30°-40° C. in vacuo in a manner such that some (about 20-30 ml) of the water is distilled off. The aqueous phase is decanted off and the oil is further processed without purification. Chromatography on silica gel with CH$_2$Cl$_2$/CH$_3$OH=95/5 gives a pure product.

R$_F$ (CH$_2$Cl$_2$/CH$_3$OH=95/5); 0.18; (CH$_2$Cl$_2$/CH$_3$OH=90/10): 0.7

H-NMR (220 MHz): δ=2.02, 1.92, 1.89 (CH$_3$—CO); and 3.03 (N-CH$_3$) ppm

EXAMPLE 11

1,3''-Bis-N-(o-nitrophenylsulphenyl)-2',3,6'-tris-(tert.-butoxycarbonyl)-2''-O-[dimethyl-(1,2-dimethyl-propyl)-silyl]-sisomicin The crude solution of 1,3''-bis-N-(o-nitrophenylsulphenyl)-2''-O-[dimethyl-(1,2-dimethylpropyl)-silyl]-sisomicin is stirred vigorously with 175 ml of a basic ion exchanger (OH$^\ominus$ form, washed with methanol), and 35 ml of tert.-butyl pyrocarbonate are added to the mixture. After 30 minutes at room temperature, the mixture is evaporated and the residue is subsequently processed without further purification. A pure product is obtained by chromatography on silica gel (running agent: $CH_2Cl_2CH_3OH=99/1$).

$R_F$ ($CH_2Cl_2/CH_3OH=98.5/1.5$): 0.31; ($CH_2Cl_2/CH_3OH=97.5/2.5$): 0.68

13-C-NMR ($CDCl_3$): δ = 102.51 (C-1''); 55.33 (C-1); 49.28 (C-3); 89.03 (C-6); 97.43 (C-1'); 47.13 (C-2'); 150.00 (C-5'); 43.00 (C-6'); 155.43 (CO); 79.66 [$(CH_3)_3C$]; 28.50 [$(CH_3)_3$—C] and 27.91 (CH—Si) ppm

EXAMPLE 12

1,3''-Bis-N-(o-nitrophenylsulphenyl)-2',3,6'-tris-(1,1-dimethyl-2,2,2-trichloro-ethoxycarbonyl)-2''-O-[dimethyl-(1,2-dimethyl-propyl)-silyl]-sisomicin 18 ml of 6 N NaOH are added to the crude solution of 1,3''-bis-N-(o-nitrophenylsulphenyl)-2''-O-[dimethyl-(1,2-dimethyl-propyl)-silyl]-sisomicin and the methanol is evaporated off in vacuo. 87 ml of methylene chloride and 78 ml of 2 N NaOH are added to the residue, and 38 ml of 1,1-dimethyl-2,2,2-trichloro-ethoxycarbonyl chloride are added dropwise at 0° C., in the course of 5 minutes. After adding 350 ml of $H_2O$, the organic phase is separated off, the aqueous phase is extracted with 350 ml of methylene chloride and the combined organic extracts are evaporated in vacuo. The oil which is obtained in a quantitative crude yield is further processed without purification. A pure sample is obtained by chromatograph on silica gel (running agent: $CH_2Cl_2/CH_3OH=99.5/0.5$).

$R_F$ ($CH_2Cl_2/CH_3OH=99.5/0.5$): 0.45

13-C-NMR ($CDCl_3$): δ = 102.59 (C-1''); 55.63 (C-1); 50.38 (C-3); 79.50 (C-4); 88.96 (C-6); 47.42 (C-2'); 97.35 (C-4'); 146.33 (C-5'); and 43.00 C-6') ppm

EXAMPLE 13

1,3''-Bis-N-(o-nitrophenylsulphenyl)-2',3,6'-tris-N-(2,2,2-trichloroethoxycarbonyl)-2''-O-[dimethyl-(1,2-dimethylpropyl)-silyl]-sisomicin 8.8 g of 1,3''-bis-N-(o-nitrophenylsulphenyl)-2''-O-[dimethyl-(1,2-dimethyl-propyl)-silyl]-sisomicin in 20 ml of methylene chloride are stirred vigorously with 24 ml of 2 N NaOH, and 5 ml of (2,2,2-trichloroethyl)-oxycarbonyl chloride are added dropwise at 0° C. The mixture is diluted with 20 ml of methylene chloride and 20 ml of $H_2O$, the aqueous phase is separated off and the organic phase is washed twice more with 10 ml of water each time, dried over $Na_2SO_4$ and evaporated in vacuo. Yield: 13.8 g (98%)

$R_F$ ($CH_2Cl_2/CH_3OH=99/1$): 0.34

EXAMPLE 14

1,3''-Bis-N-(n-nitrophenylsulphenyl)-2',3,6'-tris-N-trichloroacetyl-2''-O-[dimethyl-(1,2-dimethyl-propyl)-silyl]-sisomicin 7.5 ml of trichloroacetic anhydride are added dropwise to 8.8 g of 1,3''-bis-N-(o-nitrophenylsulphenyl)-2''-O-[dimethyl-(1,2-dimethyl-propyl)silyl]-sisomicin in 20 ml of methylene chloride/20 ml of pyridine at −15° C. and the mixture is subsequently stirred at room temperature for a further 10 minutes. After adding 20 ml of methylene chloride, the mixture is extracted by shaking twice with 20 ml of $H_2O$ each time, the organic phase is evaporated and the residue is further processed as the crude product. $R_F$ ($CH_2Cl_2/CH_3OH=97.5/2.5$)=0.72

EXAMPLE 15

1,3''-Bis-N-(o-nitrophenylsulphenyl)-2',3,6'-tris-(4-methoxybenzyloxycarbonyl)-2''-O-[dimethyl-(1,2-dimethylpropyl)-silyl]-sisomicin 3.52 g of 1,3''-bis-N-(o-nitrophenylsulphenyl)-2''-O-[dimethyl-(1,2-dimethyl-propyl)silyl]sisomicin in 10 ml of methylene chloride are stirred with 14 ml of 2 N NaOH, and 4 ml of freshly prepared 4-methoxybenzyloxycarbonyl chloride are added at 0° C. The mixture is diluted with 10 ml of methylene chloride, the aqueous phase is separated off and the organic phase is washed twice more with 10 ml of water each time, dried over $Na_2SO_4$ and evaporated in vacuo. The crude yield is 5 q (91% of theory). The product is further processed without purification. A pure product is obtained by chromatography on silica gel (running agent: $CH_2Cl_2/CH_3OH=99/1$).

$R_F$ ($CH_2Cl_2/CH_3OH=98.5/1.5$)=0.37

EXAMPLE 16

1,3''-Bis-N-(o-nitrophenylsulphenyl)-2',3,6'-tris-N-phenoxycarbonyl-2''-O-[dimethyl-(1,2-dimethyl-propyl)-silyl]-sisomicin 8.8 g of 1,3''-bis-N-(o-nitrophenylsulphenyl)-2''-O-[dimethyl-(1,2-dimethyl-propyl)-silyl]-sisomicin are dissolved in 20 ml of methylene chloride, and 17 ml of 2 N NaOH are added. 4.7 g of chloroformic acid phenyl ester are added dropwise to this emulsion at 0° C. in the course of 3 to 4 minutes. Working up is effected as in Example 15. The crude product is subsequently processed without further purification.

$R_F$ ($CH_2Cl_2/CH_3OH=97.2.5$): 0.62

EXAMPLE 17

1,3''-Bis-N-(o-nitrophenylsulphenyl)-2',3,6'-N-triacetyl-2''-O-isovaleryl-sisomicin 20 ml of acetic anhydride are added to 10 g of crude 1,3''-bis-N-(o-nitrophenylsulphenyl)-2''-O-isovaleryl-sisomicin in 30 ml of $CH_2Cl_2/20$ ml of $CH_3OH$, whilst cooling with ice, and, after 10 minutes, the mixture is evaporated in vacuo and the residue is chromatographed on a silica gel column (2.5×10 cm, running agent: $CH_2Cl_2/CH_3OH=95/5$). The yield is 5.9 g (51% of theory).

$R_F$ ($CH_2Cl_2/CH_3OH=9/1$): 0.68

13-C-NMR ($CDCl_3$): δ = 41.50 (N—$CH_3$); 70.47 (C-2''); 55.16 (C-1); 50.26 (C-3); 80.04 (C-4); 89.01 (C-6); 47.32 (C-2'); 43.13 (C-6'); 96.23 (C-1'); 171.14 and 170.26 (three CO groups); and

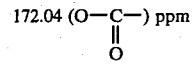

172.04 (O—C—) ppm
         ‖
         O

EXAMPLE 18

1,3''-Bis-N-(o-nitrophenylsulphenyl)-2',3,6'-triacetyl-2''-O-(2-ethyl-hexanoyl)-sisomicin 8 g of crude penta-N-(o-nitrophenylsulphenyl)-2''-O-(2-ethyl-hexanoyl)-sisomicin are converted to 1,3''-bis-N-(o-nitrophenylsulphenyl)-2''-O-(2-ethyl-hexanoyl)-sisomicin as described in Example 9, and the precipitate which has separated out is filtered off and washed twice with 7.5 ml of methanol each time. The filtrate is reacted with 5 ml of acetic anhydride in the presence of 17.5 ml of 4 N NaOH, whilst cooling with ice, and the mixture is worked up as described for Example 10. The resulting red oil is dried in vacuo and is sufficiently pure for further processing. The yield is 6 g (100% of theory).

$R_F$ (CH$_2$Cl$_2$/CH$_3$OH=9/1): 0.68

13-C-NMR (CDCl$_3$): δ=123–145 (aromatic C); 171.11 and 170.31 (3 COCH$_3$);

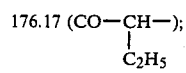

69.65 (C-2″); 99.82 (C-1″); 96.88 (C-1′); 96.57 (C-4′); 89.14 (C-6′); 70.88 (C-4″); 55.26 (C-1); and 47.46 (C-3)

EXAMPLE 19

1,3″-Bis-N-(o-nitrophenylsulphenyl)-2′,3,6′-tris-tert.-butoxycarbonyl-2″-O-(2-ethylhexanoyl)-sisomicin 40 g of crude penta-N-(o-nitrophenylsulphenyl)-2″-O-(2-ethyl-hexanoyl)-sisomicin are converted to 1,3″-bis-N-(o-nitrophenylsulphenyl)-2″-O-(2-ethyl-hexanoyl)-sisomicin as described in Example 9, and the precipitate which has separated out is filtered off and washed with 170 ml of methanol. 125 ml of a basic ion exchanger (OH$^\ominus$ form, Lewatit ® MP 500 rinsed with methanol) and 25 g of di-tert.-butyl dicarbonate are added to the filtrate, the mixture is stirred vigorously for 1 hour and filtered and the filtrate is evaporated in vacuo. 35 g (99% of theroy) are obtained.

$R_F$ (CH$_2$Cl$_2$/CH$_3$OH=97.5/2.5)=0.59

IR (KBr): 1,705 cm$^{-1}$

EXAMPLE 20

1,3″-Bis-N-(o-nitrophenylsulphenyl)-2′,3,6′-N-triacetyl-sisomicin

Starting from 1,3″-bis-N-(o-nitrophenylsulphenyl)-2′,3,6′-triacetyl-2″-O-[dimethyl-(1,2-dimethyl-propyl)-silyl]-sisomicin The unpurified oil obtained according to Example 10 is dissolved in 100 ml of dimethylsulphoxide (DMSO), 8.75 ml of a 50 percent strength aqueous KF solution are added and the mixture is stirred vigorously. After 2 hours, the mixture is poured onto 300 g of ice, the precipitate is allowed to settle and the aqueous DMSO phase is decanted carefully. The residue is stirred with 100 ml of water, the aqueous phase is decanted and the residue is dried under a high vacuum. 28 g (76%, relative to penta-N-(o-nitrophenylsulphenyl)-2″-O-[dimethyl-(1,2-dimethylpropyl)-silyl]-sisomicin according to Example 2) of crude product are obtained, which can be further purified by chromatography on silica gel with CH$_2$Cl$_2$/CH$_3$OH=95/5.

(b) From 1,3″-bis-N-(o-nitrophenylsulphenyl)-2′,3,6′-N-triacetyl-2″-O-(2-ethylhexanoyl)-sisomicin The crude oil from Example 18 is dissolved in 14 ml of methylene chloride/37.5 ml of CH$_3$OH and the solution is left to stand with 25 ml of 6 N NaOH at room temperature for 48 hours. After distilling off the organic solvent in vacuo, the oil obtained is washed twice with a little water and dried. 3.75 g (71%, relative to penta-N-(o-nitrophenylsulphenyl)-2″-O-(2-ethylhexanoyl)-sisomicin according to Example 3) are obtained.

(c) From 1,3″-bis-N-(o-nitrophenylsulphenyl)-2′,3,6′-N-triacetyl-2″-O-isovaleryl-sisomicin 5.9 g of the compound obtained according to Example 17 are reacted and worked up according to Example 20 b. 4.89 g (91% of theory) are obtained.

(d) From 1,3″-bis-N-(o-nitrophenylsulphenyl)-sisomicin 7.52 g of the substance obtained according to Example 21 are acetylated with acetic anhydride and 4 N NaOH. The crude product obtained after the working up is isolated in quantitative yield (8.7 g).

All the physical data of the products prepared according to a–d are identical.

$R_F$ (CH$_2$Cl$_2$/CH$_3$OH=9/1): 0.37

1-H-NMR (220 MHz) in CD$_3$OD: δ=1.97, 1.94 and 1.88 (CH$_3$CO): and 3.03 (3″-N-CH$_3$) ppm 13-C-NMR (CD$_3$OD): δ=173.0 and 173.42 (three CH$_3$CO) ppm

EXAMPLE 21

1,3″-Bis-N-(o-nitrophenylsulphenyl)-sisomicin (a) 18.5 g of 1,3″-bis-N-(o-nitrophenylsulphenyl)-2″-O-[dimethyl-(1,3-dimethyl-propyl)-silyl]-sisomicin are dissolved in 50 ml of dimethylsulphoxide, and 5.4 ml of 4 N NaOH are added. After 5 minutes, the mixture is poured onto 500 ml of H$_2$O and the precipitate is filtered off and dried in vacuo. The yield is 14.7 g (93% of theory).

(b) 17.6 g of 1,3″-bis-N-(o-nitrophenylsulphenyl)-2″-O-[dimethyl-(1,3-dimethyl-propyl)-silyl]-sisomicin in 60 ml of dimethylsulphoxide and 5 ml of water are stirred vigorously with 20 g of KF for 18 hours and the mixture is worked up as under (a). 14 g (93% of theory) are obtained.

(c) The crude product from Example 35 is dissolved in 5 ml of CH$_2$Cl$_2$ and 11 ml of CH$_3$OH and the solution is left to stand with 2.6 ml of 6 N NaOH at room temperature for 2 hours. The reaction mixture is evaporated, the residue is introduced onto a column (7 cm long, 5.5 cm wide) filled with silica gel and the column is eluted with 1. CH$_2$Cl$_2$, 2. CH$_2$Cl$_2$/CH$_3$OH 95/5, 3. CH$_2$Cl$_2$/CH$_3$OH 8/2 and 4. CH$_2$Cl$_2$/CH$_3$OH/20% strength aqueous NH$_3$ 7/2.7/0.3. 3.42 g (46% of theory, relative to crude penta-N-(o-nitrophenylsulphenyl)-sisomicin) are obtained.

(d) The crude product from Example 36 is reacted and worked up analogously to Example 21 c. 3.5 g (47% of theory, relative to crude penta-N-(o-nitrophenylsulphenyl)-sisomicin) are obtained. $R_F$ (running agent as Example 6): 0.16

13-C-NMR (DMSO-d6): δ=124–147 (aromatic C); 70.58 (C-2″), 34.66 (N—CH$_3$); 55.95 (C-1); 49.02 (C-3); 85.84 (C-4); and 86.79 (C-6) ppm

EXAMPLE 22

1,3″-Bis-N-(o-nitrophenylsulphenyl)-2′,3,6′-tris-(tert.-butoxycarbonyl)-sisomicin (a) From 1,3″-bis-N-(o-nitrophenylsulphenyl)-2′,3,6′-tris-N-(tert.-butoxycarbonyl-2″-O-[dimethyl-(1,2-dimethylpropyl)-silyl]-sisomicin The crude product from Example 11 is dissolved in 87 ml of dimethylsulphoxide, 10 g of powdered KF and 5 ml of H$_2$O are added and the mixture is stirred vigorously. After 3 hours, the mixture is diluted with 300 ml of H$_2$O and the precipitate is filtered off, washed with water and dried. The crude yield is quantitative.

$R_F$ (CH$_2$Cl$_2$/CH$_3$OH=95/5) 0.48

(b) From 1,3''-bis-N-(o-nitrophenylsulphenyl)-2',3,6'-tris-N-tert.-butoxycarbonyl-2''-O-(2-ethyl-hexanoyl)-sisomicin The crude product from Example 19 is dissolved in 300 ml of $CH_3OH$/60 ml of $CH_2Cl_2$, the solution is left to stand with 60 ml of 4 N NaOH at room temperature for 3 days, the methanol is evaporated off in vacuo, the residue is taken up in methylene chloride and the mixture is extracted by shaking three times with water. The organic phase is dried over $Na_2SO_4$ and evaporated. The yield is 18.1 g (57% of theory).

EXAMPLE 23

1,3''-Bis-N-(o-nitrophenylsulphenyl)-2',3,6'-tris-N-(1,1-dimethyl-2,2,2-trichloroethoxycarbonyl)-sisomicin The crude 1,3''-N-(o-nitrophenylsulphenyl)-2',3,6'-tris-(1,1-dimethyl-2,2,2-trichloroethoxycarbonyl)-2''-O-[dimethyl-(1,2-dimethyl-propyl)-silyl]-sisomicin from Example 12 is dissolved in 90 ml of dimethylsulphoxide and the solution is stirred with 8 ml of water and 5 g of KF for 4 hours. The reaction mixture is diluted with 300 ml of toluene and the dimethylsulphoxide is extracted by shaking with a total of 500 ml of water. After drying and evaporating the organic phase, the yellow residue is further processed without purification.

$R_F$ ($CH_2Cl_2/CH_3OH=97.5/2.5$)=0.42

EXAMPLE 24

1,3''-Bis-N-(o-nitrophenylsulphenyl)-2',3,6'-tris-N-(4-methoxybenzyloxycarbonyl)-sisomicin 5 g of the crude product from Example 15 are dissolved in 12 ml of dimethylsulphoxide and 1 ml of water and the solution is stirred with 0.9 g of KF at room temperature for 4 hours. The mixture is diluted with 50 ml of methylene chloride and the dimethylsulphoxide is extracted by shaking 3 times with 10 ml of water each time. The crude product which remains after evaporating the organic phase is subsequently processed without further purification.

$R_F$ ($CH_2Cl_2/CH_3OH=95/5$)=0.52

EXAMPLE 25

1,3''-Bis-N-(o-nitrophenylsulphenyl)-2',3,6'-tris-N-(2,2,2-trichloroethoxycarbonyl)-sisomicin 11 g of the crude product from Example 13 are dissolved in 24 ml of dimethylsulphoxide and 1.3 ml of water and the solution is stirred with 0.6 g of KF for 1 hour. The product is precipitated with $H_2O$ and dried in vacuo. The yield is 98% of theory.

$R_F$ ($CH_2Cl_2/CH_3OH=97.5/2.5$)=0.32

EXAMPLE 26

1,3''-Bis-N-(o-nitrophenylsulphenyl)-2',3,6'-tris-N-trichloroacetyl)-sisomicin

The crude oil from Example 14 is dissolved in 20 ml of dimethylsulphoxide, 2 ml of a 50 percent strength KF solution are added and the mixture is stirred vigorously for 3 hours. The product is precipitated with water and is washed with water and dried. The crude product is subsequently processed without further purification.

$R_F$ ($CH_2Cl_2/CH_3OH=97.5/2.5$)=0.42

13-C-NMR ($CDCl_3$): $\delta$=103.60 (C-1''); 66.48 (C-3''); 55.15 (C-1); 50.60 (C-3;) 79.86 (C-4); 76.18 (C-5); 89.16 (C-6); 97.74 (C-1'); 96.84 (C-4'); 149.80 (C-5); 92.78 ($CCl_3$); 162.29 and 162.11 (CO) ppm.

EXAMPLE 27

3''-N-(o-Nitrophenylsulphenyl)-2',3,6'-tris-N-acetyl-sisomicin 28 g of the crude product from Example 20 are dissolved in 56 ml of methylene chloride, 18 g of 2-mercaptobezthiazole and 93 ml of methanol are added and the mixture is shaken vigorously until a clear solution has formed. The mixture is kept at 5° C. for 20 hours and 16 ml of 12 percent strength $H_2O_2$ solution are added dropwise. The precipitate is filtered off and the filtrate is evaporated in vacuo. A red foam which can be employed for most of the subsequent reactions without further purification is obtained. The yield is 26.8 g (88.6%, relative to crude penta-N-(o-nitrophenylsulphenyl)-2''-O-[dimethyl-(1,2-dimethyl-propyl)-silyl]-sisomicin according to Example 2). The foam consists of the desired product to the extent of 57%, that is to say the total yield, relative to Example 2, is 51% of theory. For further purification, 3 g of the crude product are chromatographed on silica gel [column: 3.8×30 cm, running agent: $CH_2Cl_2/CH_3OH=9/1$ with increasing addition (finally 5%) of a mixture of $CH_2Cl_2/CH_3OH$/20% strength aqueous $NH_3=2/4/1$]. The yield is 1.4 g.

$R_F$ ($CH_2Cl_2/CH_3OH$/20% strength aqueous $NH_3=7.5:2.4:0.15$): 0.79

13-C-NMR (d6-DMSO): 71.70 (C-2''); 50.89 (C-1); 47.73 (C-3); 80.95 (C-4); 74.79 (C-5); 86.53 (C-6); 45.52 (C-2'); 96.55 (C-1'); 146.78 (C-5'); and 169.23, 168.94 and 169.64 (3×CO) ppm

EXAMPLE 28

3''-N-(o-Nitrophenylsulphenyl)-2',3,6'-tris-N-tert.-butoxycarbonyl-sisomicin

The crude product from Example 22 (a) is dissolved in 89 ml of methylene chloride, the solution is shaken vigorously with 30 g of 2-mercaptobenzthiazole and 250 ml of methanol until a clear solution is obtained and the solution is left to stand at 5° C. for 28 hours. After filtering off the precipitate, the filtrate is evaporated rapidly in vacuo, the residue is taken up in toluene and the mixture is extracted with 4 N NaOH until the 2-mercaptobenzthiazole has been completely removed. After drying the organic phase over $Na_2SO_4$, the solvent is evaporated off in vacuo. The residue (25.1 g ≙ 67% over all the stages, starting from Example 2) is sufficiently pure for further reactions.

$R_F$ ($CH_2Cl_2/CH_3OH$/20% strength aqueous $NH_3$ 93/6.5/0.5)=0.49

EXAMPLE 29

3''-N-(o-Nitrophenylsulphenyl)-2',3,6'-tris-N-(1,1-dimethyl-2,2,2-trichloro-ethoxycarbonyl)sisomicin The reaction is carried out analogously to Example 28, starting from the crude product of Example 23. The evaporation residue obtained gives, after chromatograph on silica gel (running agent $CH_2Cl_2/CH_3OH=95/5$), 21.7 g (43%, relative to Example 2) of pure end product.

$R_F$ ($CH_2Cl_2/CH_3OH=95/5$): 0.22; ($CH_2Cl_2/CH_3OH=90/10$): 0.77

13-C-NMR ($CDCl_3$):=70.68 (C-2''); 38.41 (N—$CH_3$); 50.87 (C-1); 50.53 (C-3); 79.81 (C-4); 89.94 (C-6); 98.24 (C-1'); 47.45 (C-2'); 97.52 (C-4'); 146.35 (C-5'); and 42.35 (C-6') ppm

EXAMPLE 30

3″-N-(o-Nitrophenylsulphenyl)-2′,3,6′-tris-N-(p-methoxybenzyloxycarbonyl)-sisomicin The crude product from Example 24 is dissolved in 19 ml of methylene chloride and the solution is shaken with 20 ml of methanol and 4.9 g of 2-mercaptobenzthiazole until a clear solution is obtained. After 3 days at 5° C., the precipitation is filtered off, the filtrate is evaporated and the residue is chromatographed on silica gel (column 3.5×11 cm, running agent: initially $CH_2Cl_2/CH_3OH=97.5/2.5$, finally $CH_2Cl_2/CH_3OH=95/5$). The yield of pure product is 2.1 g (52%, relative to Example 15).

$R_F$ ($CH_2Cl_2/CH_3O$]/20% strength aqueous $NH_3$ 93/6.5/0.5)=0.49

EXAMPLE 31

3″-N-(o-Nitrophenylsulphenyl)-2′,3,6′-tris-N-trichloroacetyl-sisomicin

The product from Example 26 is dissolved in 13 ml of methylene chloride, the solution is shaken with 26 ml of methanol and 5 g of 2-mercaptobenzthiazole until a clear solution is obtained, and this solution is left to stand at 5° C. for 3 days. The precipitate is filtered off, the filtrate is evaporated and the residue is chromatographed on silica gel (running agent a: $CH_2Cl_2/CH_3OH=95/5$); b: $CH_2Cl_2/CH_3OH/20$% strength aqueous $NH_3=93/6.5/0.5$. $R_F$ ($CH_2Cl_2/CH_3OH/20$% strength aqueous $NH_3=93/6.5/0.5$): 0.43

13-C-NMR ($CDCl_3$):=103.43 (C-1″); 67.46 (C-3″); 50.85 (C-1); 50-28 (C-3); 79.44 (C-4); 76.51 (C-5); 89.29 (C-6); 97.61 (C-1′); 96.62 (C-4′); 149.50 (C-5′); 92.46 and 92.38 (C-4′); and 162.01 and 161.76 (CO) ppm.

EXAMPLE 32

3″-N-(o-Nitropehnylsulphenyl)-2′,3,6′-tris-N-(2,2,2-trichloroethoxycarbonyl)-sisomicin 9.8 g of the crude product from Example 25 are dissolved in 9 ml of methylene chloride, the solution is shaken with 16 ml of methanol and 1.45 g of 2-mercaptobenzthiazole until a clear solution is obtained, and this solution is then left to stand at room temperature for 6 days. The precipitation is filtered off and the filtrate is chromatographed on silica gel (running agent as in Example 31).

$R_F$ (running agent b from Example 31): 0.53

EXAMPLE 33

Penta-N-(o-nitrophenylsulphenyl)-2″-O-(2,2,-dimethylhexyloxycarbonyl)-sisomicin 4.3 ml of triethylamine and 1 g of p-dimethylaminopyridine are added to 12 g of crude penta-N-(o-nitrophenylsulphenyl)-sisomicin in 50 ml of absolute methylene chloride, and 5.8 ml of 2,2-dimethylhexyloxycarbonyl chloride are added at 0° C. and the mixture is stirred at room temperature for 40 hours. The reaction mixture is washed twice with 15 ml of saturated $NaNCO_3$ solution each time and dried over sodium sulphate and petroleum ether is added to precipitate the desired product. After drying, the yield is quantitative.

$R_F$ ($CH_2Cl_2/CH_3OH$ 99/1)=0.57

EXAMPLE 34

Penta-N-(o-nitrophenylsulphenyl)-2″-O-(2,2-dimethylpropoxycarbonyl)- sisomicin 12 g of crude penta-N-(o-nitrophenylsulphenyl)-sisomicin are reacted with 6 ml of 2,2-dimethylpropoxycarbonyl chloride and the mixture is worked up, analogously to Example 33. The product is isolated in quantitative yield.

$R_F$ ($CH_2Cl_2/CH_3$ 99/1)=0.53

EXAMPLE 35

1,3″-Bis-N-(o-nitrophenylsulphenyl)-2″-O-(2,2,-dimethylhexyloxycarbonyl)-sisomicin The crude product from Example 33 is shaken with 18 ml of methylene chloride, 26 ml of methanol and 3.7 g of 2-mercaptobenzthiazole until a clear solution is formed and the solution is left to stand at room temperature for 70 hours. The solid obtained after filtering off the precipitate formed and evaporating the filtrate has a $R_F$ value ($CH_2Cl_2/CH_3OH/20$% strength aqueous $NH_3$ 7/2.7/0.3) of 0.61 and is subsequently processed according to Example 21c without further purification.

EXAMPLE 36

1,3″-Bis-N-(o-nitrophenylsulphenyl)-2″-O-(2,2-dimethylpropoxycarbonyl)-sisomicin From the crude product from Example 34, analogously to Example 35, a solid with a $R_F$ value ($CH_2Cl_2/CH_3OH/20$% strength aqueous $NH_3$ 7/2.7/0.3) of 0.62 is obtained, which is further processed according to Example 21d.

EXAMPLE 37

1-(2-Aminoethoxycarbonyl)-sisomicin (a) 4-Nitrophenyl 2-(o-nitrophenylsulphenylamino)-ethyl carbonate A solution of 1.4 g of 2-aminoethanol in 30 ml of dioxane is initially introduced and a solution of 3.8 g of o-nitrophenylsulphenic acid chloride in 10 ml of dioxane, and 8.5 ml of 2 N sodium hydroxide solution are simultaneously added dropwise, whilst maintaining a pH of 8. After stillring the mixture at room temperature for several hours, it is concentrated in vacuo, the residue is taken up in ethyl acetate and the mixture is washed twice with water, dried with $Na_2SO_4$ and concentrated in vacuo. The oil which remains is chromatographed over 100 g of silica gel with toluene/ethyl acetate (2:1) and the main component is separated off. Yield: 2.9 g of N-(2-hydroxyethyl)-o-nitrosulphenic acid amide.

456 mg of this compound and 600 mg of chloroformic acid p-nitrophenyl ester are dissolved in 5 ml of acetonitrile, and 300 mg of triethylamine in 5 ml of acetonitrile are added, whilst cooling with ice. After one hour at room temperature , the mixture is concentrated in vacuo, the residue is taken up in 30 ml of methylene chloride, the mixture is extracted twice with water, dried with $Na_2SO_4$ and concentrated in vacuo, the resulting oil is chromatographed over 100 g of silica gel with toluene/ethyl acetate (2:1) and the main fraction is separated off. Yield: 250 ml of an orange oil which slowly crystallises completely.

IR (KBr): 1,770 $cm^{-1}$; $R_F$ value toluene/ethyl acetate (2:1): 0.77.

(b) 5 g of 3″-N-(o-nitrophenylsulphenyl)-2′,3,6′-tris-N-trichloroacetylsisomicin are dissolved in 10 ml of pyridine, and 2.2 g of the crude product from Example 37(a) are added. After 2 hours, the mixture is evaporated in vacuo, the residue is taken up in 30 ml of methylene chloride/30 ml of methanol and 10 ml of 4 NaOH are added. After 4 hours, the mixture is again evaporated in vacuo, 1.7 g of 2-mercaptobenzthiazole in 10 ml of methylene chloride/3 ml of methanol are added and the mixture is acidified carefully with half-concentrated methanolic HCl. After adding 10 ml of water, the mixture is brought to pH 10 with a basic ion exchanger (Lewatit MP 500, OH$^\ominus$ form), the aqueous phase is separated off, the organic phase is evaporated and the residue is chromatographed on silica gel (running agent: $CH_2Cl_2/CH_3OH/20\%$ strength aqueous $NH_3=2/4/1$). The yield is 1,930 mg (75% of theory).

$R_F=0.28$ ($CH_2Cl_2/CH_3OH/20\%$ strength aqueous $NH_3$ 2/4/1).

EXAMPLE 38

1-N-[(S,R,R)-2,3,4,5-Tetrahydroxypentyl]-sisomicin 1 g of 2′,3,6′-tri-N-acetyl-3″-N-(o-nitrophenylsulphenyl)-sisomicin is dissolved in 33 ml of methanol and 6.6 ml of water. 1 g of D-xylose is added and the mixture is heated to 70° C. for 30 minutes. After adding 330 mg of sodium cyanoborohydride, the mixture is heated for a further hour, left to cool and deionised by stirring with a basic ion exchanger resin (OH$^\ominus$ form ®Lewatit MP 500 (Bayer AG, Leverkusen)). The mixture is evaporated in vacuo to give an amorphous solid.

In oder to split off the protective groups, the solid is heated under reflux in 6 ml of saturated barium hydroxide solution for 5 hours. The barium ions are removed by adding sulphuric acid until the pH is 5 and then centrifuging the mixture. The centrifugate is deionised by stirring thoroughly with a basic ion exchanger resin (OH$^\ominus$ form ®Lewatit MP 500 (Bayer AG, Leverkusen)) and, is washed with 150 ml of methylene chloride and then extracted by stirring with wood charcoal. The mixture is filtered and the filtrate is evaporated in vacuo to give a colourless solid. $R_F$ value=0.3 (running agent system: $CH_2Cl_2/CH_3OH/$ concentrated $NH_3=2/2/1$).

EXAMPLE 39

1-N-Ethyl-sisomicin 364 mg of 2′,3,6′-tri-N-acetyl-3″-N-(o-nitrophenylsulphenyl)-sisomicin in 3 ml of water are stirred with a solution of 25 μl of acetaldehyde in 1.5 ml of methanol at room temperature for 30 minutes. 100 mg of sodium cyanoborohydride are then added and, after a further hour, 3 μl of acetaldehyde in 0.2 ml of methanol are added. After one hour, the mixture is evaporated in vacuo, the residue is treated, in 10 ml of water, with a basic ion exchanger resin (OH$^-$ form ®Lewatit MP 500 (Bayer AG, Leverkusen)) and, after filtering off the resin, the filterate is evaporated to dryness in vacuo. In order to split off the protective groups, the substance is heated to the reflux temperature in 2 ml of saturated barium hydroxide solution for 5 hours. The mixture is worked up as in Example 38 and 1-N-ethyl-sisomicin is obtained as a colourless, amorphous solid.

We claim:

1. A compound of the formula

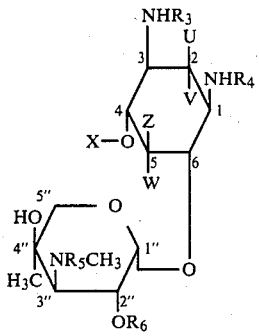

in which

X denotes a radical of the formula

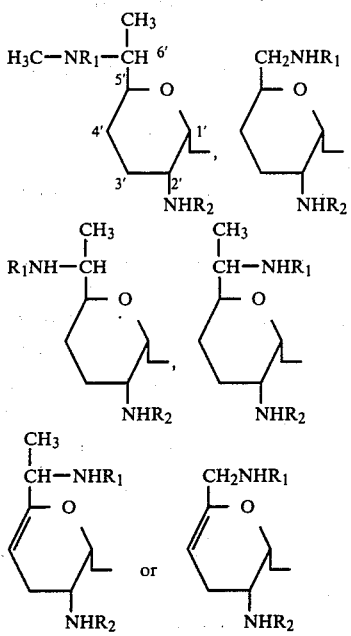

U, V, W and Z independently denote a hydrogen atom or a hydroxyl group,

U, V, and W and Z not simultaneously denoting OH, $R_1$, $R_2$, and $R_3$ denote —CO—A, $R_4$ denotes a hydrogen atom, $R_5$ denotes a radical —$SR_7$ and $R_6$ denotes a hydrogen atom or a space-filling substituent which can be split off of the formula

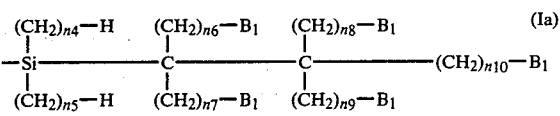

or

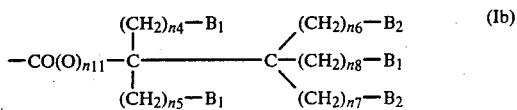

in which $n_4$, $n_5$, $n_6$, $n_7$, $n_8$, $n_9$ and $n_{10}$ are independently 0, 1, 2 or 3, $n_{11}$ is 0 or 1, $B_2$ has any of the meanings given for B or denotes a $C_1$ to $C_5$ alkoxy or $C_3$ to $C_5$ alkenyloxy group and $B_1$ has any of the meanings given for B, and in which A denotes a radical of the formulae

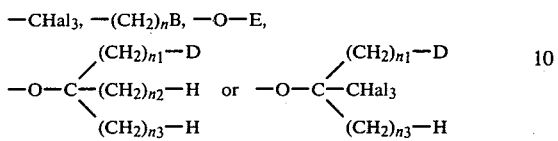

wherein

B and D denote a hydrogen atom or a phenyl group which is optionally monosubstituted or disubstituted by nitro, halogen, $C_1$ to $C_4$ alkyl, $C_1$ to $C_4$ alkoxy or phenyl, E denotes a phenyl group which is optionally monosubstituted or disubstituted by nitro, halogen, $C_1$ to $C_4$ alkyl, $C_1$ to $C_4$ alkoxy or phenyl, n is 0, 1, 2, 3, 4 or 5, $n_1$, $n_2$ and $n_3$ are independently 0, 1, 2, 3, 4 or 5, Hal denotes a fluorine, chlorine or bromine atom and $R_7$ denotes a phenyl, diphenylmethyl or triphenylmethyl group which is optionally monosubstituted to trisubstituted by $CF_3$, $NO_2$, $C_1$ to $C_4$ alkyl, $C_1$ to $C_4$ alkoxy- ($C_1$ to $C_4$ alkoxy )-carbonyl or phenyl or monosubstituted to pentasubstituted by halogen.

2. A compound according to claim 1 in which $R_6$ denotes a hydrogen atom or a radical of the formula

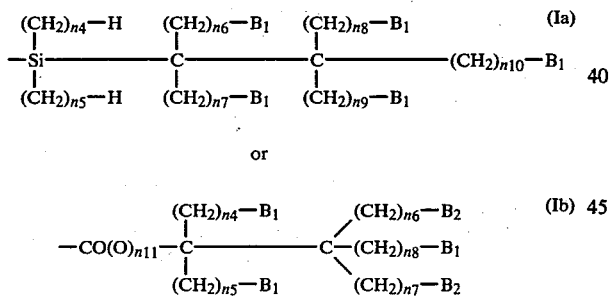

$n_4$, $n_5$, $n_6$, $n_7$, $n_8$, $n_9$ and $n_{10}$ are independently 0, 1, 2 or 3, $n_{11}$ is 0 or 1, $B_2$ has any of the meanings given for $B_1$ or denotes a $C_1$ to $C_5$ alkoxy or $C_3$ to $C_5$ alkenyloxy group, $B_1$ denotes a hydrogen or phenyl group which is optionally monosubstituted or disubstituted by nitro, halogen, $C_1$ to $C_4$ alkyl, $C_1$ to $C_4$ alkoxy or phenyl, 3. A compound according to claim 1 or 2 in which D and E independently denote a hydrogen or phenyl group which is optionally unsubstituted or disubstituted by nitro, halogen, $C_1$-$C_4$-alkyl, $C_1$ to $C_4$ alkoxy or phenyl.

4. A compound according to claim 1, of the formula

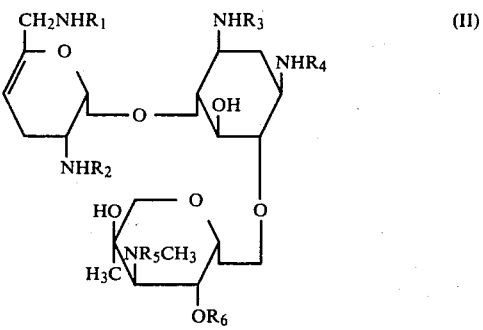

in which $R_1$, $R_2$, $R_3$, $R_4$, $R_5$ and $R_6$ have the same meanings as in claim 1.

5. A compound according to claim 2, in which $B_1$ in radical (Ia) denotes a hydrogen atom or $B_1$ and $B_2$ in radical (Ib) have the same meaning.

6. A process for the production of compounds as claimed in claim 1, which comprises (1) reacting a compound of the formula

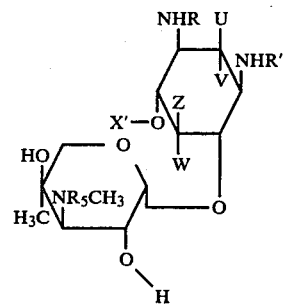

in which

X' denote a radical of the formulae

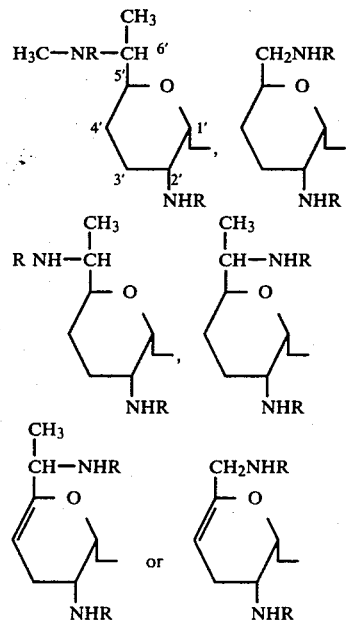

R and R' denote a radical $-SR_7$ and

U, V, W, Z, $R_5$ and $R_7$ have the same meanings as in claim 1, with a silylating agent or an acylating agent of the formula $$R_8-G$$

in which $R_8$ denotes a space filling substituent which can be split off of the formula

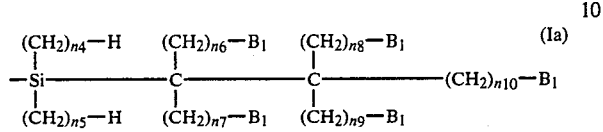

or

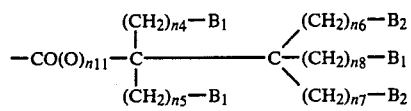

in which $n_4$, $n_5$, $n_6$, $n_7$, $n_8$, $n_9$ and $n_{10}$ are independently 0, 1, 2 or 3, $n_{11}$ is 0 or 1, $B_2$ has any of the meanings given for B or denotes a $C_1$ to $C_5$ alkoxy or $C_3$ to $C_5$ alkenyloxy group and $B_1$ has any of the meanings given for B, B denoting a hydrogen atom or a phenyl group which is optionally monosubstituted or disubstituted by nitro, halogen, $C_1$ to $C_4$ alkyl, $C_1$ to $C_4$ alkoxy or phenyl, and G denotes a leaving group for this reaction step, (2) splitting off the radicals R, (3) acylating the amino groups liberated in step (2) with an acylating agent of the formula $$A-CO-G'$$

in which

A has the same meaning as in claim 1 and

G' denotes a leaving group for the acylation, (4) splitting off the radical R' and, optionally, (5) splitting off the space-filling substituent $R_8$.

7. A process according to claim 6, in which step (1) is carried out in the presence of an inert solvent or, if the acylating agent is an acid anhydride or activated ester, in the presence of a basic solvent.

8. A process according to claim 6 or 7, in which step (1) is carried out at a temperature of 0° to 80° C. or, if the acylating agent is an acid halide, at a temperature of 0° to 40° C.

9. A process according to claim 6, 7 or 8, in which step (2) is carried out at a temperature of 0° to 20° C. in an organic solvent or mixture of organic solvents.

10. A process according to claim 6, in which step (5) is carried out in a water-immiscible organic solvent using a tetraalkylammonium fluoride or in a dimethylsulphoxide/water mixture either using an inorganic fluoride or an inorganic base.

11. A process according to claim 6 in which $R_8$ is dimethyl-ethyl silyl.

* * * * *